US00PP33342P2

(12) United States Plant Patent
Sierra

(10) Patent No.: US PP33,342 P2
(45) Date of Patent: Aug. 10, 2021

(54) ***LAMIUM* PLANT NAMED 'NONNOGARDK'**

(50) Latin Name: *Lamium maculatum*
Varietal Denomination: Nonnogardk

(71) Applicant: Hortech, Inc., Nunica, MI (US)

(72) Inventor: Richard Sierra, Fruitport, MI (US)

(73) Assignee: HORTECH, INC., Spring Lake, MI (US)

( * ) Notice: Subject to any disclaimer, the term of this patent is extended or adjusted under 35 U.S.C. 154(b) by 0 days.

(21) Appl. No.: 17/033,705

(22) Filed: Sep. 26, 2020

(51) Int. Cl.
*A01H 5/02* (2018.01)
*A01H 6/50* (2018.01)

(52) U.S. Cl.
USPC ..... Plt./444

(58) Field of Classification Search
USPC ..... Plt./444
See application file for complete search history.

*Primary Examiner* — Susan McCormick Ewoldt
(74) *Attorney, Agent, or Firm* — Penny J. Aguirre

(57) ABSTRACT

A new cultivar of *Lamium* plant named 'Nonnogardk' that characterized by its variegated leaves with silver centers and green margins, its leaves that are an average of 5.1 cm in length and 3.2 cm in width, its plant size that is an average of 15.24 cm in height and 91 cm in spread, its flowers that are clear pink in color, and its flowers that bloom in May and June with a rebloom with less flowers in September and October in Michigan.

1 Drawing Sheet

Botanical classification: *Lamium maculatum.*
Variety denomination: 'Nonnogardk'.

BACKGROUND OF THE INVENTION

The present invention relates to a new and distinct cultivar of *Lamium* plant, botanically known as *Lamium maculatum* 'Nonnogardk' and will be referred to hereinafter by its cultivar name, 'Nonnogardk'. The new cultivar of *Lamium* is a new cultivar of spotted dead nettle; a hardy herbaceous perennial grown for landscape and ground cover use.

'Nonnogardk' was discovered by the Inventor in June of 2019 as a naturally occurring branch mutation of *Lamium maculatum* 'Purple Dragon' (U.S. Plant Pat. No. 15,890) that was grown outdoors in a container block in Nunica, Mich.

Asexual propagation of the new cultivar was first accomplished by stem cuttings in June 2019 under the direction of the Inventor in Nunica, Mich. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Nonnogardk' as a unique cultivar of *Lamium.*

1. 'Nonnogardk' exhibits variegated leaves with silver centers and green margins.
2. 'Nonnogardk' exhibits leaves that are an average of 5.1 cm in length and 3.2 cm in width.
3. 'Nonnogardk' exhibits a plant size an average of 15.24 cm in height and 91 cm in spread.
4. 'Nonnogardk' exhibits flowers that are clear pink in color.

5. 'Nonnogardk' exhibits flowers that bloom in May and June with a rebloom with less flowers in September and October in Michigan.

The parent plant, 'Purple Dragon', is similar to 'Nonnogardk' in plant vigor and growth habit but differs from 'Nonnogardk' in having flowers that are purple in color. 'Nonnogardk' can be most closely compared to the *Lamium maculatum* varieties 'Pink Pewter' (not patented) and 'Orchid Frost' (U.S. Plant Pat. No. 11,122). 'Pink Pewter' is similar to 'Nonnogardk' in having pink flowers, similar leaves, and similar plant height and spread. 'Pink Pewter' differs from 'Nonnogardk' in having green margins that are not as broad on older leaves and in having a less vigorous and slower growth habit. 'Orchid Frost' is similar to 'Nonnogardk' in having leaves with a similar shape and coloration and having a similar plant height. 'Orchid Frost' differs from 'Nonnogardk' in having flowers that are rosy pink in color.

BRIEF DESCRIPTION OF THE DRAWING

The accompanying colored photograph illustrates the overall appearance and distinct characteristics of the new *Lamium*. The photograph was taken of a one-year-old plant as grown outdoors in a garden in Nunica, Mich. The photograph provides a view of the flowers and leaves of 'Nonnogardk'. The colors in the photograph may differ slightly from the color values cited in the detailed botanical description, which accurately describe the colors of the new *Lamium.*

DETAILED BOTANICAL DESCRIPTION

The following is a description of a 9-month-old plant as grown outdoors in #1 trade containers in Nunica, Mich. The phenotype of the new cultivar may vary with variations in environmental, climatic, and cultural conditions, as it has not been tested under all possible environmental conditions.

The color determination is in accordance with The 2015 Colour Chart of The Royal Horticultural Society, London, England, except where general color terms of ordinary dictionary significance are used.

General description:

*Blooming period*.—Blooms in May and June and reblooms with less flowers in September and October in Michigan.

*Plant habit*.—Herbaceous perennial, mounded plant habit, flowering stems emerging from basal leaves.

*Height and spread*.—Average of 20 cm in height and 35 cm in spread as a 1-year-old plant in a 2-liter container and an average of 15.24 cm in height and 91 cm in spread as a mature plant in the landscape.

*Cold hardiness*.—At least in U.S.D.A. Zone 3.

*Diseases and pests*.—No susceptibility or resistance to diseases or pests has been observed.

*Root description*.—Fibrous and fine, 160C in color.

*Root development*.—Time required for root initiation is an average of 2 weeks, time required to produce a young plant from a rooted cutting is an average of 8 weeks.

*Propagation*.—Stem cuttings.

*Growth rate*.—Moderately vigorous.

Stem description:

*Shape*.—Quadrangular.

*Stem color*.—Young; 142A, mature; 144A.

*Stem size*.—Up to 30 cm in length, average of 3 mm in diameter, secondary branches average of 6 cm in length, 2 cm in diameter.

*Stem surface*.—Ridged with vertical ridges, sparsely covered with fine pubescence up to 0.5 mm in length, NN155C in color.

*Branching habit*.—Average of 20 main basal branches, primarily emerge from base with some smaller secondary branches, up to 4 per main branch.

Foliage description:

*Leaf division*.—Simple.

*Leaf arrangement*.—Opposite.

*Leaf shape*.—Broadly ovate.

*Leaf size*.—Average of 3.7 cm in length, up to 3 cm in width.

*Leaf number*.—Average of 28 per main branch 30 cm in length, secondary branches have an average of 10 per branch 6 cm in length.

*Leaf base*.—Cordate.

*Leaf apex*.—Ranges between acute and obtuse.

*Leaf margins*.—Serrate.

*Leaf venation*.—Reticulate, recessed on upper surface and raised on lower surface, color matches leaf color, moderately covered with very fine pubescent hairs an average of 0.3 mm in length and NN155C in color.

*Leaf surface*.—Upper and lower surface is sparsely covered with very fine pubescent hairs, average of 0.3 mm in length and ranges between NN155C in color and slightly indistinguishable matching leaf surface color.

*Leaf internode length*.—Average of 2 cm.

*Leaf color*.—Young upper surface; 145B, base 145D, tip and margins 145A, young lower surface 145A, mature upper surface; variegated, center of the leaf to the base 194A, margins 137B, mature lower surface; 138A.

*Petiole*.—Average of 1 cm in length and 2 mm in length, upper and lower color; center 145A, outside edges 143A, both surfaces slightly glossy and densely covered with long thin woolly hairs; up to 1 mm in length and NN155C in color to slightly translucent.

*Foliage fragrance*.—Slightly mint-like when crushed.

Flower description:

*Inflorescence type*.—Verticillasters (dense whorls) of galeate flowers.

*Lastingness of inflorescence*.—Individual flowers last 3 to 4 days, inflorescence lasts about 10 days.

*Inflorescence size*.—Verticillasters are about 2 cm in diameter and 4 cm in diameter.

*Flower type*.—Zygomorphic and galeate.

*Flower number*.—Average of 20 flowers per verticillaster produced on upper axillary nodes.

*Flower fragrance*.—Pungent (typical of species).

*Flower buds*.—Oblong and globose in shape, about 4 mm in length and 2 mm in diameter, color; N155B and 49B.

*Flower size*.—About 2.5 cm in length and about 5 mm in diameter.

*Peduncles*.—None, sessile.

*Calyx*.—5-pointed, star-shaped, divergent, about 6 mm in length and 5 mm in width, persistent.

*Sepals*.—5, primarily fused with un-fused portion somewhat spreading with free portion about 2 mm in width and 3 mm in length, 144A and 144B in color, surfaces are glabrous, base is fused, apiculate apex, entire margin.

*Petals*.—2 lipped with upper lip; galeate and curved like a hood, broadly obovate in shape with a round apex, base is truncate and fused to lower lip, margin is entire and slightly wavy, glabrous surface, color of outer surface is a blend of 63B and 63C and color of inner surface a blend of 62C and N155B, fading to 167A in color, 1.3 cm in height and 2 mm in width, lower lip; fused into tube at base with 2 lateral lobes and a front lobe having two kidney-shaped sections that face downward, lateral lobes; about 5 mm in length and diameter, glabrous surface, margins entire with a linear appendage about 2 mm in length and 0.3 mm in width on each lateral lobe, color of outer surface is a blend of 63B and 63C, color of inner surface a blend of 62C and N155B and fading to N78A, front lobe has a glabrous surface, entire margins, kidney shaped, about 2 mm in height and 3 mm in width, color is a blend of N155B and 62B, tube; 3 mm in length and 2 mm in width, glabrous and satiny surface and N155B to NN155D in color.

Reproductive organs:

*Gynoecium*.—Pistil; 1, style; average of 1.3 cm in length, NN155D in color, stigma; bi-fid, 2 mm in length, pointed apex, NN155C in color, ovary is superior, about 1.5 mm in diameter and 195B in color in color.

*Androecium*.—4 stamens, filaments; average of 1.4 cm in length, NN155C in color, anthers; oblong in shape, basifixed, 2 mm in diameter, 1.5 mm in depth, 179A in color, pollen is abundant and 28A in color.

*Fruit*.—Fruit and seed production were not observed.

It is claimed:

1. A new and distinct cultivar of *Lamium* plant designated 'Nonnogardk' as described and illustrated herein.

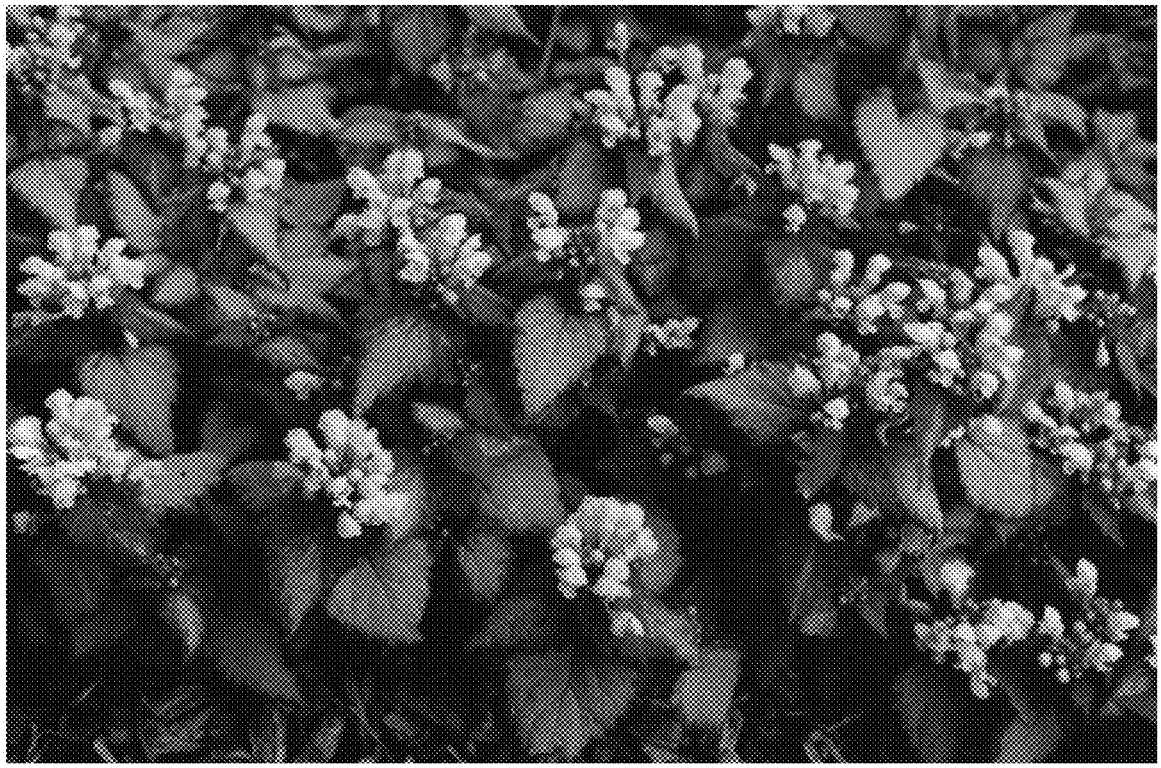

* * * * *